United States Patent [19]

Pellico

[11] Patent Number: 5,071,637

[45] Date of Patent: Dec. 10, 1991

[54] FOAMABLE FLUORIDE COMPOSITIONS AND METHOD

[76] Inventor: Michael A. Pellico, 3024 Military Ave., Los Angeles, Calif. 90272

[21] Appl. No.: 418,251

[22] Filed: Oct. 6, 1989

[51] Int. Cl.$^5$ .......................... A61L 9/04; A61K 7/18; A61C 5/00

[52] U.S. Cl. ......................................... 424/45; 424/52; 433/215; 433/217.1; 106/35

[58] Field of Search .............................. 424/45, 49, 52; 433/215, 217.1; 106/35

[56] References Cited

U.S. PATENT DOCUMENTS

| | | | |
|---|---|---|---|
| 4,137,303 | 1/1979 | Gaffar et al. | 424/52 |
| 4,601,898 | 7/1986 | Stier et al. | 424/52 |
| 4,770,634 | 9/1988 | Pellico | 433/217.1 |

Primary Examiner—Nathan M. Nutter
Attorney, Agent, or Firm—Donald Diamond

[57] ABSTRACT

A foamable fluoride composition, for use in dental therapy, is provided that contains water, dental fluoride, foaming agent and acidifying agent. An illustrative composition comprises water, sodium fluoride, hydrofluoric acid, ethoxylated polyoxypropylene adduct of propylene glycol and phosphoric acid. The foamable fluoride composition, which is packaged in a nonmetallic, acid resistant, aerosol container in combination with an aerosol propellant, is dispensed into the trough of a dental tray as a dense, stable, non-flowable foam which is superimposed about and into engagement with the teeth to be treated to thereby effect fluoride uptake by the dental enamel. The fluoride foam provides substantially the same fluoride uptake as a fluoride gel but this result is achieved by the fluoride foam with substantially less fluoride in the tray than that which is present in a corresponding tray containing a like volume of fluoride gel.

18 Claims, No Drawings

FOAMABLE FLUORIDE COMPOSITIONS AND METHOD

BACKGROUND OF THE INVENTION

This invention relates to dental compositions and, more particularly, to foamable fluoride compositions which are adapted to provide stable foams for use in dental therapy.

It is generally understood in the dental art that certain kinds of food decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associated with the plaque, cause decalcification beneath the plaque matrix through metabolic activity which results in the accumulation and localized concentration of organic acids. The etching and decalcification of the enamel may continue until the pulp chamber of the tooth is reached.

Fluoride compounds have been incorporated into dental topicals and into consumables to provide an orally beneficial effect by reducing the dissolving action of acids on dental enamel. It has been reported that the fluoride combines with hydroxyapatite, the crystalline structure of the teeth, to produce a modified crystalline structure which is more resistant to acid attack.

Diverse fluoride compounds have been disclosed in the prior art for use in dental care including, for example, sodium fluoride, sodium monofluorophosphate, stannous fluoride, fluoroalkyl phosphates, and quaternary ammonium fluorides.

The fluorides can be incorporated into gels, rinses, toothpaste, tooth powder, chewing gum and the like for topical application. Fluoride treatment can also be undertaken through consumables such as fluoridated drinking water and fluoride tablets. Heretofore, fluoride gels have been used in dental practice to topically apply fluoride to the teeth. The fluoride gel is usually supplied as a thick gel in a plastic bottle from which it is dispensed into the trough of a plastic dental tray that is inserted into the mouth in juxtaposition to the teeth whereby the teeth engage the gel for about 1 to 4 minutes, as per the supplier's instructions.

A typical fluoride gel contains water, a water soluble dental fluoride such as sodium fluoride, glycerol, an acidifying agent such as phosphoric acid, and a water soluble thickener such as carboxymethyl cellulose, polyvinyl alcohol, or xanthan gum.

An illustrative fluoride gel formulation is as follows:

| INGREDIENTS | PARTS BY WEIGHT |
| --- | --- |
| Water | 85.5 |
| Sodium fluoride | 2.7* |
| Xanthan gum | 3.2 |
| Glycerol | 3.4 |
| Phosphoric acid (85%) | 4.1 |

*Available fluoride 1.2 pts. by wt.

The water soluble thickener is selected so as to provide a highly viscous and thick system for maintaining the gel in the tray and in positive contact with the teeth, since a thin gel would tend to flow away from the tooth surface and thereby reduce fluoride uptake by the tooth and, additionally, a thin gel could flow out of the tray and cause the patient to gag and choke.

The acidifying agent is selected so as to provide the fluoride gel with a pH between about 3.0 and 4.5 which facilitates and enhances fluoride uptake by the teeth.

There are several problems associated with the use of fluoride gels in dental therapy. One of the most vexing problems is that of viscosity. The fluoride gel must be thick enough so that it does not flow out of the dental tray while the tray is in the patient's mouth and, at the same time, the gel must be thin enough to be dispensed from a plastic bottle into the tray in preparation for the fluoride treatment. Because it is extremely difficult to formulate a fluoride gel that flows from a plastic dispensing bottle and yet remains stationary in the dental tray for up to 4 minutes while in the mouth, the fluoride gels heretofore available had a tendency to flow while in the tray and cause patient gagging during the course of treatment.

Another problem associated with fluoride gels is that of toxicity. Fluorides have a low concentration threshold for exerting toxic effects. It is reported that severe symptons can be manifested from the ingestion of less than one gram of sodium fluoride. Thus, the ingestion of any significant amount of fluoride gel can produce serious consequences. This risk is especially noteworthy because fluoride gels, which have been flavored to mask the acidic taste, are most often used to treat children and the flavoring can increase the chance of unintentionally swallowing a significant amount of the semi-fluid gel.

A further problem associated with fluoride gels is the cost-effectiveness of the thick gel. In view of the high viscosity of the fluoride gels, the only fluoride which is available for uptake by the tooth is that which is in the immediate vicinity of the tooth surface. The remaining fluoride, which is the bulk of the fluoride in the tray, is unavailable for dental uptake because fluoride movement is restricted by the high viscosity of the gel.

Accordingly, it would be advantageous to provide a tray-fluoride that is non-flowable and which requires substantially less fluoride in the tray to achieve the same fluoride uptake as a corresponding volume of fluoride gel.

SUMMARY OF THE INVENTION

In accordance with one aspect of this invention, there is provided a foamable fluoride composition comprising:
  (a) a water soluble dental fluoride in an amount to provide the composition with about 0.5 to about 5 wt.% available fluoride;
  (b) an orally compatible and acid stable foaming agent in an amount from about 4 to about 20 wt.%;
  (c) an orally compatible and acid stable foam-wall thickener in an amount from about 2 to about 20 wt.%;
  (d) an orally compatible acidifying agent in an amount to provide the composition with a pH from about 3.0 to about 4.5; and
  (e) water to 100 wt.%.

In accordance with a second aspect of this invention, there is provided a method for treating teeth with a fluoride foam, which comprises:

(a) dispensing a pressurized and foamable fluoride composition from an aerosol container into the trough of a dental tray to form a fluoride foam within the trough, wherein the foamable fluoride composition contains: a water soluble dental fluoride in an amount to provide the composition with about 0.5 to about 5 wt.% available fluoride; an orally compatible and acid stable foaming agent in an amount from about 4 to about 20 wt.%; an orally compatible and acid stable foam-wall thickener in an amount from about 2 to about 20 wt.%; an orally compatible acidifying agent in an amount to provide the composition with a pH from about 3.0 to about 4.5; and water to 100 wt.%; and (b) superimposing the trough of the dental tray and its fluoride foam content about and into engagement with the teeth to be treated to effect fluoride uptake by such teeth.

DETAILED DESCRIPTION

The foamable fluoride compositions of this invention comprise aqueous solutions containing water soluble dental fluoride, foaming agent, foam-wall thickener, and acidifying agent.

Illustrative water soluble dental fluorides which can be used in the practice of this invention include sodium fluoride, sodium monofluorophosphate, stannous fluoride, fluoroalkyl phosphate salts as described in U.S. Pat. No. 2,955,985 (Kuna, 1960) such as monammonium 1,1,7 - trihydroperfluoroheptyl phosphate, quaternary ammonium fluorides as described in U.S. Pat. No. 3,124,512 (Schmidt et al., 1964) such as doceyltrimethyl-ammonium fluoride, and mixtures thereof. The dental fluoride is generally present in the foamable fluoride composition in an amount to provide the composition with about 0.5 to about 5 wt.% available fluoride and, preferably, in an amount to provide the composition with about 1.0 to about 2.5 wt.% available fluoride. Sodium fluoride is particularly well suited for use in fluoride foam therapy and, when so used, is generally present in the foamable fluoride composition in an amount from about 1.1 to about 11.1 wt.% and, preferably in an amount from about 2.2 to about 5.6 wt.%.

Foaming agents which can be used in the practice of this invention to produce dense, stable, non-flowable foams are those which are orally compatible and acid stable and include, for example, sucrose monostearate, sucrose distearate, sodium lauryl sulfate and mixtures thereof. The foaming agent is generally present in the foamable fluoride composition in an amount from about 4 to about 20 wt.% and, preferably, in an amount from about 7 to about 13 wt.%.

Foam-wall thickeners which can be used in the practice of this invention to produce foams having enhanced stability are those which are orally compatible and acid stable and include, for example, glycerol, sorbitol, hydrogenated starch hydrolysate (a polyol) available under the trademark Hystar TPF from Lonza, Inc., Fair Lawn, N.J. 07410 as a 70% solution, and mixtures thereof. The foam-wall thickener is generally present in the foamable fluoride composition in an amount from about 2 to about 20 wt.% and, preferably, in an amount from about 4 to about 15 wt.%.

Acidifying agents which can be used in the practice of this invention to facilitate and enhance fluoride uptake by the tooth structure from the fluoride foam are those which are orally compatible and include, for example, phosphoric acid, citric acid and mixtures thereof. The acidifying agent is generally present in the foamable fluoride composition in an amount to provide the aqueous solution with a pH from about 3.0 to about 4.5.

The foamable fluoride compositions are prepared by blending dental fluoride, foaming agent, foam-wall thickener and acidifying agent with water under mild mixing conditions at ambient temperature. The resulting aqueous solution is added in a predetermined amount to an open-mouth aerosol container. An appropriate aerosol valve is fitted over the mouth of and secured to the container. The container is then charged through the aerosol valve with an aerosal propellant, such as propane, isobutane or a mixture thereof as, for example, a mixture of 4% propane and 96% isobutane, to an operating pressure of about 40 pounds per square inch gage. A dispensing actuator and spout assembly is then fitted onto the valve.

In use, the aerosol container, with its pressurized and foamable fluoride composition, is shaken and rotated to align the dispensing spout with the trough of a dental tray and the actuator is pressed to dispense an amount of flouride foam that substantially fills the volume defined by the trough. The tray is then placed in a patient's mouth so as to superimpose the trough and its fluoride foam content about and into engagement with the teeth to be treated. The fluoride foam, which is dense, stable and non-flowable, is maintained in engagement with the teeth for about 1 to 4 minutes to effect fluoride uptake by the teeth.

| INGREDIENTS | PARTS BY WEIGHT |
| --- | --- |
| Water | 85.0 |
| Sodium fluoride | 3.1 |
| Sucrose distearate | 4.0 |
| Glycerol | 2.2 |
| Phosphoric acid (85%) | 5.0 |
| Flavor | q.s. |

The above formulation has a pH of about 3.0 and produces a foam having excellent density and stability characteristics.

| INGREDIENTS | PARTS BY WEIGHT |
| --- | --- |
| Water | 79.0 |
| Sodium fluoride | 3.1 |
| Sucrose monostearate | 10.1 |
| Glycerol | 2.2 |
| Phosphoric acid (85%) | 4.8 |
| Flavor | q.s. |

The above formulation produces a foam which is lighter than the foam produced by Examples 1(a) through 1(c).

| INGREDIENTS | PARTS BY WEIGHT |
| --- | --- |
| Water | 85.0 |
| Sodium fluoride | 3.1 |
| Sodium lauryl sulfate | 3.0 |
| Glycerol | 3.2 |
| Phosphoric acid (85%) | 5.0 |
| Flavor | q.s. |

The above formulation produces a dense foam but it does not last as long as the foams produced by Examples 1(a) through 1(c).

| INGREDIENTS | PARTS BY WEIGHT |
| --- | --- |
| Water | 85.5 |
| Stannous fluoride | 5.0 |
| Sucrose monostearate | 3.0 |
| Glycerol | 3.1 |
| Phosphoric acid (85%) | 4.0 |
| Flavor | q.s. |

| INGREDIENTS | PARTS BY WEIGHT |
| --- | --- |
| Water | 71.5 |
| Dodecyl-trimethyl-ammonium fluoride | 12.5 |
| Sucrose monostearate | 8.0 |
| Citric acid | 8.0 |
| Flavor | q.s. |

EXAMPLE II

A comparative study was undertaken to evaluate fluoride uptake by dental enamel from (a) the fluoride foam of this invention, (b) a commercial fluoride gel for professional use available under the trademark Nupro APF Gel, and (c) deionized water.

The foamable fluoride precursor for the fluoride foam contained 3.1 wt.% sodium fluoride, 6.0 wt.% sucrose distearate, 2.0 wt.% glycerol, 4.0 wt.% phosphoric acid (85%), 1.0 wt.% cherry flavor and water to 100 wt.%. The fluoride precursor was added to an open-mouth aerosol container and the final aerosol dispensing package was completed and pressurized in a customary manner as hereinabove described.

The results of the comparative study are set forth in the following table:

TABLE I

| GROUP | TREATMENT | FLUORIDE UPTAKE | |
| --- | --- | --- | --- |
| | | PPM | DEPTH |
| 1 | Deionized water | 374 ± 38 | 1.16 ± 0.12 |
| 2 | Fluoride foam | 4210 ± 332 | 0.80 ± 0.07 |
| 3 | Nupro APF Gel | 4333 ± 318 | 1.08 ± 0.14 |

The comparative study shows that the fluoride uptake from the fluoride foam and from the fluoride gel is substantially the same.

The weight ratio of fluoride gel to fluoride foam, on a like volume basis, is about 2.5 to 1. Accordingly, the weight of fluoride in a dental tray substantially filled with fluoride foam is somewhat less than one-half the weight of fluoride in a like tray substantially filled with fluoride gel, where the percent of fluoride in each system is substantially the same. Thus, the fluoride foam of this invention provides substantially the same fluoride uptake as fluoride gel but this result is achieved by the fluoride foam with significantly less fluoride in the tray which markedly reduces exposure to fluoride toxicity in fluoride-tray treatment.

ALTERNATIVE EMBODIMENT

In an alternative emobodiment, an orally stable and acid compatible nonionic surfactant in the form of a block copolymer of polyoxypropylene and polyoxyethylene can be employed as the foaming agent and, when so employed, a foam wall thickener such as glycerol or sorbitol is not required to obtain a foamable fluoride composition that produces a dense, stable, non-flowable foam.

The block copolymer which can be utilized in this embodiment of the invention can be prepared by initially creating a hydrophobe of desired molecular weight through the controlled addition of propylene oxide to the two hydroxyl groups of propylene glycol and thereafter ethylene oxide is added to sandwich the hydrophobe between polyoxyethylene hydrophillic groups which are controlled by length to constitute a selected percentage (by weight) of the final molecule. The resulting block copolymer comprises an ethoxylated polyoxypropylene adduct of propylene glycol. In general, the block copolymers which can be used in this aspect of the invention have an average molecular weight from about 3,000 to about 15,000, with an intermediate average molecular weight being from about 6,000 to about 15,000, and a preferred average molecular weight being from about 10,000 to about 15,000. The ethoxylated portion of the block copolymer generally constitutes from about 30 to about 80 percent, by weight, of the molecule, with an intermediate percentage being from about 40 to about 80 percent, by weight, of the molecule, and a preferred percentage being from about 70 to about 80 percent, by weight, of the molecule. A particularly preferred block copolymer is an ethoxylated polyoxypropylene adduct of propylene glycol wherein the composition has an average molecular weight of about 12,600, the polyoxypropylene portion thereof has a molecular weight of about 4,000, and the ethoxylated portion thereof constitutes about 70 percent, by weight, of the molecule.

In this embodiment of the invention, the nonionic, block copolymer, foaming agent is generally present in the foamable fluoride composition in an amount from about 2.5 to about 11 wt.% and, preferably, in an amount from about 3.5 to about 8 wt.%.

Block copolymer surfactants, which have the above described structural characteristics, are available from BASF Corporation, Chemicals Division, 100 Cherry Hill Road, Parsippany, N.J. 07054. Functional properties of the block copolymers, including foaming characteristics, are extensively described in the BASF technical brochure entitled Pluronic & Tetronic Surfactants (1987). Specific examples of nonionic surfactants which are useful in the practice of this embodiment of the invention, and which comprise polyoxyethylene/polyoxypropylene block copolymers, are set forth in the following table:

TABLE I

| Proprietary name | Average mol. wt. | Polyoxyethylene wt. % | HLB |
| --- | --- | --- | --- |
| Pluronic L64 | 2,900 | 40 | 12–18 |
| Pluronic P123 | 5,750 | 30 | 7–12 |
| Pluronic F108 | 14,600 | 80 | >24 |
| Pluronic F127 | 12,600 | 70 | 18–23 |

The following examples illustrate various ingredients and concentrations which can be used in the preparation of foamable fluoride compositions that incorporate block copolymer, nonionic surfactants as the foaming agent.

| Ingredients | Parts by Weight |
| --- | --- |
| Water | 178.75 |
| Sodium Fluoride | 4.71 |
| Phosphoric Acid | 4.50 |
| Hydrofluoric Acid | 0.23 |
| Pluronic F127 | 11.25 |

-continued

| Ingredients | Parts by Weight |
| --- | --- |
| Sodium Saccharin | 0.27 |
| Flavor | 0.50 |

The above formulation produces a very stable, dense, non-flowable foam.

EXAMPLE II

| Ingredients | Parts by Weight |
| --- | --- |
| Water | 168.00 |
| Sodium Fluoride | 4.71 |
| Phosphoric Acid | 4.50 |
| Hydrofluoric Acid | 0.23 |
| Pluronic F127 | 21.00 |
| Sodium Saccharin | 0.27 |
| Flavor | 0.50 |

The above formulation produces a very stable, dense, non-flowable foam which, however, has a noticeable detergent taste.

EXAMPLE III

| Ingredients | Parts by Weight |
| --- | --- |
| Water | 184.00 |
| Sodium Fluoride | 4.71 |
| Phosphoric Acid | 4.50 |
| Hydrofluoric Acid | 0.23 |
| Pluronic F108 | 5.25 |
| Sodium Saccharin | 0.27 |
| Flavor | 0.50 |

The above formulation produces a fluoride foam having minimum foam stability for use as a tray material in dental therapeutics.

As an adjunct to the water soluble fluoride, the fluoride foam compositions advantageously contain hydrofluoric acid in an amount from about 0.05 to about 0.20 wt.% and, preferably, in an amount from about 0.07 to 0.15 wt.%.

Heretofore, it has been common to package aerosol compositions in tin or aluminum containers having a coated inner surface which insulates the compositions from the metal surface. As long as the protective coating has no pin holes and is uniformly applied to the inner surface of the container, the coated containers can be used for holding diverse aerosol compositions, including acidic compositions. However, in normal production, a large number of the coated containers will have pin holes in the coating and/or thin coating areas. Since the foamable fluoride can have a pH of about 3.3 and can contain both phosphoric acid and hydrochloric acid, any defect in the protective coating can lead to an accelerated acidic attack on the metallic can which can result in leakage or explosion.

In accordance with another aspect of this invention, it has been found that the acidic fluoride foam compositions can be advantageously packaged in aerosol containers comprising polyester resin such as polyethylene terephthalate, which containers are resistant to acidic reaction and, therefore, do not require a protective coating. By employing a polyethylene terephthalate bottle as the aerosol container for the acidic fluoride foam, the quality of the dispensed foam is substantially improved.

The prior art discloses that liquid oral care preparations can be formulated with a fluoride composition such as sodium fluoride and with nonionic surfactants such as Pluronic surfactants.

U.S. Pat. No. 4,137,303 (Gaffar, et al., 1979) discloses in an antibacterial antiplaque mouthwash which may also contain a surface active agent and/or a fluoride-providing compound. The patentees, in an illustrative embodiment, disclose a mouthwash formulation containing flavored alcohol, Pluronic F-108, glycerine, benzethonium chloride, sodium saacharin, a polyamine polyphosphonic compound and water, with the pH adjusted to 8.0.

U.S. Pat. No. 4,601,898 (Stier, et al., 1986) discloses an anti-caries mouthrinse containing titanium tetrafluoride stabilized with a chelating agent such as citric acid and which can be further formulated with alcohol, a humectant such as glycerin or aqueous sorbitol, and surfactants including cationic, anionic and nonionic surfactants. The patentees, in an illustrative embodiment, disclose a mouthrinse formulation containing titanium tetrafluoride, sodium citrate, Pluronic F-127, flavor, dye, sodium saacharin and water.

In contrast to the flowable liquid compositions of the prior art, the compositions and method of the alternative embodiment described herein provide a dense, stable, non-flowable fluoride foam which is adapted for use as a tray material for professional applications in dental therapeutics.

The water soluble fluorides which can be used in the alternative embodiment include sodium fluoride, sodium monofluorophosphate and mixtures thereof in an amount to provide the composition with about 0.5 to about 5 wt.% available fluoride. The orally compatible acidifying agent which can be used in the alternative embodiment comprises phosphoric acid in an amount to provide the composition with a pH from about 3.0 to about 4.5.

In view of the foregoing description and examples, it will become apparent to those of ordinary skill in the art that equivalent modifications thereof may be made without departing from the spirit and scope of this invention.

That which is claimed is:

1. A foamable fluoride composition for pressurized dispensing into the trough of a dental tray as a dense, stable, non-flowable foam, consisting essentially of:
   (a) a water soluble dental fluoride in an amount to provide the composition with about 0.5 to about 5 wt.% available fluoride;
   (b) an orally compatible and acid stable nonionic foaming agent comprising an ethoxylated polyoxypropylene adduct of propylene glycol having an average molecular weight from about 3,000 to about 15,000 and the ethoxylated portion thereof constitutes from about 30 to about 80 percent, by weight, of the molecule, said nonionic foaming agent being present in an amount from about 2.5 to about 11 wt.%;
   (c) an orally compatible acidifying agent in an amount to provide the composition with a pH from about 3.0 to about 4.5;
   (d) hydrofluouric acid in an amount from about 0.05 to about 0.20 wt.%; and
   (e) water to 100 wt.%.

2. The composition of claim 1 wherein the dental fluoride is a member selected from the group consisting of sodium fluoride, sodium monofluorophosphate and mixtures thereof.

3. The composition of claim 2 wherein the dental fluoride is sodium fluoride.

4. The composition of claim 1 wherein the ethoxylated polyoxypropylene adduct of propylene glycol has an average molecular weight from about 6,000 to about 15,000 and the ethoxylated portion thereof constitutes from about 40 to about 80 percent, by weight, of the molecule.

5. The composition of claim 1 wherein the ethoxylated polyoxypropylene adduct of propylene glycol has an average molecular weight from about 10,000 to about 15,000 and the ethoxylated portion thereof constitutes from about 70 to about 80 percent, by weight, of the molecule.

6. The composition of claim 1 wherein the ethoxylated polyoxypropylene adduct of propylene glycol has an average molecular weight of about 12,600, the polyoxypropylene portion thereof has a molecular weight of about 4,000 and the ethoxylated portion thereof constitutes about 70 percent, by weight, of the molecule.

7. The composition of claim 1 wherein the acidifying agent is phosphoric acid.

8. The composition of claim 1 wherein the concentration of nonionic foaming agent is from about 3.5 to about 8 wt %.

9. The composition of claim 1 wherein (a) the dental fluoride is sodium fluoride in an amount from about 2.2 to about 5.6 wt.%, (b) hydrofluoric acid is present in an amount from about 0.07 to about 0.15 wt.%, (c) the ethoxylated polyoxypropylene adduct of propylene glycol foaming agent has an average molecular weight of about 12,600, the polyoxypropylene portion thereof has a molecular weight of about 4,000 and the ethoxylated portion thereof constitutes about 70 percent, by weight, of the molecule, said foaming agent being present in an amount from about 3.5 to about 8 wt.%, and (d) the acidifying agent is phosphoric acid.

10. The composition of claim 1 in pressurized combination with an aerosol propellant and disposed within a dispensing aerosol container comprising an acid resistant polyester resin.

11. A method for treating teeth with a fluoride foam, which consist essentially of:
(a) dispensing a pressurized and foamable fluoride composition from an acid resistant aerosol container into the trough of a dental tray to form a fluoride foam within said trough, said foamable fluoride composition containing:
a water soluble dental fluoride in an amount to provide the composition with about 0.5 to about 5 wt.% available fluoride;
an orally compatible and acid stable nonionic foaming agent comprising an ethoxylated polyoxypropylene adduct of propylene glycol having an average molecular weight from about 3,000 to about 15,000 and the ethoxylated portion thereof constitutes from about 30 to about 80 percent, by weight, of the molecule, said nonionic foaming agent being present in an amount from about 2.5 to about 11 wt.%;
an orally compatible acidifying agent in an amount to provide the composition with a pH from about 3.0 to about 4.5;
hydrofluoric acid in an amount from about 0.05 to about 0.20 wt.%; and
water to 100 wt.%; and
(b) superimposing the trough of the dental tray and its fluoride foam content about and into engagement with the teeth to be treated to effect fluoride uptake by such teeth.

12. The method of claim 11 wherein the dental fluoride is a member selected from the group consisting of sodium fluoride, sodium monofluorophosphate and mixtures thereof.

13. The method of claim 12 wherein the dental fluoride is sodium fluoride.

14. The method of claim 11 wherein said ethoxylated polyoxypropylene adduct of propylene glycol has an average molecular weight from about 6,000 to about 15,000 and the ethoxylated portion thereof constitutes from about 40 to about 80 percent, by weight, of the molecule.

15. The method of claim 11 wherein said ethoxylated polyoxypropylene adduct of propylene glycol has an average molecular weight from about 10,000 to about 15,000 and the ethoxylated portion thereof constitutes from about 70 to about 80 percent, by weight, of the molecule.

16. The method of claim 11 wherein nonionic foaming agent has an average molecular weight of about 12,600, the polyoxypropylene portion thereof has a molecular weight of about 4,000, and the ethoxylated portion thereof constitutes about 70 percent, by weight, of the molecule.

17. The method of claim 11 wherein the acidifying agent is phosphoric acid.

18. The method of claim 11 wherein the (a) the dental fluoride is sodium fluoride in an amount from about 2.2 to about 5.6 wt.%, (b) hydrofluoric acid is present in an amount from about 0.07 to about 0.15 wt.%, (c) the ethoxylated polyoxypropylene adduct of propylene glycol foaming agent has an average molecular weight of about 12,600, the polyoxypropylene portion thereof has a molecular weight of about 4,000 and the ethoxylated portion thereof constitutes about 70 percent, by weight, of the molecule, said foaming agent being present in an amount from about 3.5 to about 8 wt.%, and (d) the acidifying agent is phosphoric acid.

* * * * *